United States Patent [19]

Kubela et al.

[11] 3,980,674

[45] Sept. 14, 1976

[54] 2,3-DISUBSTITUTED 7-OXABICYCLO-[2.2.1]-5-HEPTENE

[75] Inventors: Rudolf Kubela, Cote St. Luc; Lise A. Hughes, Ville de Lery, both of Canada

[73] Assignee: Delmar Chemicals Limited, Ville LaSalle, Canada

[22] Filed: Jan. 28, 1974

[21] Appl. No.: 437,162

[52] U.S. Cl. .................. 260/347.3; 260/247.2 R; 260/268 BC; 260/293.58; 260/326.36
[51] Int. Cl.² ....................................... C07D 307/00
[58] Field of Search ................... 260/347.3

[56] References Cited

UNITED STATES PATENTS

| 2,576,082 | 11/1953 | Tischler | 71/88 |
| 2,637,640 | 5/1953 | Tischler | 71/75 |

*Primary Examiner*—Natalie Trousof
*Assistant Examiner*—Bernard Dentz
*Attorney, Agent, or Firm*—Christen & Sabol

[57] ABSTRACT

The present invention is concerned with novel 7-oxabicyclo-[2.2.1]-5-heptene derivatives and a process for their production. These compounds are useful intermediates in the production of various pharmacologically active compounds.

6 Claims, No Drawings

ND674

2,3-DISUBSTITUTED 7-OXABICYCLO-[2.2.1]-5-HEPTENE

BACKGROUND OF THE INVENTION

The present invention relates to novel 2,3-disubstituted 7-oxabicyclo-[2.2.1]-5-heptene derivatives useful as intermediates in the production of pharmacologically active compounds and processes for the production of such derivatives.

PRIOR ART

Adducts of the general formula I:

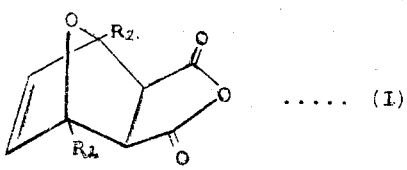

wherein $R_1$ and $R_2$ each individually represent hydrogen atoms or alkyl groups, are known and may be produced by reacting furan or a 2- or 2,5-alkyl derivative thereof with maleic anhydride in a classic Diels-Alder reaction. The exo-compounds of formula I above represent only one of the two possible sets of isomers, there also being the corresponding set of endo-compounds. If the Diels-Alder reaction is effected in an aprotic solvent, it is found that the predominant product, i.e. the product obtained in the highest yield, is the aforementioned exo-isomer (See, for example, R. Woodward and H. Baer, J. Am. Chem. Soc. 70, 1161 [1948]).

It is also known that the anhydride ring in such adducts may be opened with water using sodium hydroxide as a catalyst, to form the disodium salt of the corresponding di-acid, or with sodium methoxide in methanol to give the monomethyl ester monosodium salt of the corresponding di-acid.

SUMMARY OF INVENTION

It has now been found that the anhydride ring of such Diels-Alder adducts may be opened with an amine to produce novel mono amine- and if desired inorganic-salts which are useful intermediates in the preparation of pharmacologically active compounds.

It is an object of the present invention to provide novel 2,3-disubstituted 7-oxabicyclo-[2.2.1]-5-heptene derivatives and a process for the production thereof.

In its compound aspect, the present invention provides novel derivatives of the general formula II:

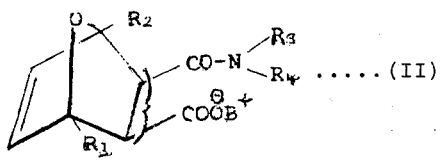

wherein
$R_1$ and $R_2$ each individually represent hydrogen atoms or alkyl groups, preferably lower alkyl groups;
$R_3$ and $R_4$ each individually represent hydrogen atoms, alkyl groups or, together with the adjoining nitrogen atom from a heterocyclic ring which may include further heteroatoms such as oxygen, and nitrogen; and $B^+$ represents an organic or inorganic cation.

The compounds of the present invention are intermediates useful in the production of pharmacologically active compounds. In particular, they are useful in the preparation of pharmacologically active cyclo-pentane and pentene derivatives described in detail below after Example 12 (in the table on page 9).

The term "lower alkyl" as used throughout this specification means alkyl groups containing from 1 to 6, preferably from 1 to 4, carbon atoms; for example, methyl, ethyl, propyl, isopropyl and the various butyl, pentyl and hexyl radicals. Alkyl groups $R_3$ and $R_4$ may also be substituted by a phenyl group.

The cyclic groups represented by

are typically of the formula:

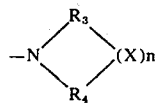

wherein
$R_3$ and $R_4$ are individually alkylene groups, preferably the same groups and containing 2 or 3 carbon atoms.
X is O or N, and
$n$ is zero or 1.
Examples of such cyclic groups are:
piperazinyl (i.e., $R_3=R_4=-C_2H_4-$; X=N; $n=1$)
pyrrolidinyl (i.e., $R_3+R_4=-(CH_2)_4-$; $n=0$)
morpholinyl (i.e., $R_3=R_4=-C_2H_4-$; X=O; $n=1$) and
piperidinyl (i.e., $R_3+R_4=-(CH_2)_5$; $n=0$).

$B^+$ represents an inorganic or organic cation, preferably a monovalent cation. Examples of inorganic monovalent cations include the alkali metal cations such as lithium, potassium and sodium, especially the latter.

Possible polyvalent inorganic cations are barium and calcium. Examples of monovalent amine residues include those residues of amines of the formula:

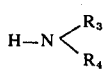

where $R_3$ and $R_4$ are defined above.
Possible polyvalent organic cations include those obtained from diamines such as ethylenediamine.

In a further aspect the present invention provides a process for the production of the novel salts of formula II defined above, said process comprising reacting an adduct of the general formula I:

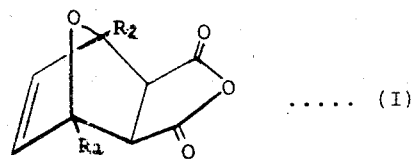

wherein $R_1$ and $R_2$ are as defined for formula II, with at least two moles of an amine of the general formula III:

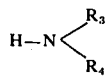

wherein $R_3$ and $R_4$ are as defined for formula I, and, if desired, converting the amine salt so formed into an inorganic salt by known methods.

Generally, conversion from an amine to an inorganic salt is effected by simple exchange such as treatment with an inorganic base for example, an alkali metal alkoxide, hydroxide, carbonate, etc. such as the potassium and sodium compounds, the alkoxides being preferred.

It will be noted that formula III includes within its scope ammonia and for the purposes of this specification ammonia is deemed to be an amine.

In the above compounds, $R_1$ and $R_2$ may be the same or different. If $R_1$ and $R_2$ are the same, the starting adduct of formula I is symmetric and upon opening the anhydride ring only one enantiomeric pair is obtained. The possible enantiomers, are of formulae IIa and IIb.

II a

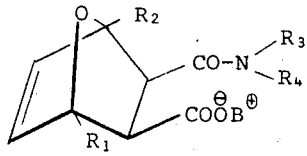

II b

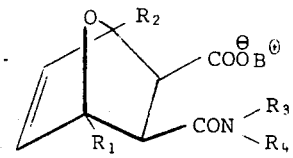

wherein $R_1$ to $R_4$ and $B^+$ are as defined above, and $R_1 = R_2$.

However, when $R_1$ is not the same as $R_2$ in the starting adduct, opening of the anhydride ring results theoretically in two enantiomeric pairs. It is not felt necessary to draw out the actual structures of the four possible isomers since one skilled in the art would have little difficulty in doing so, if desired, especially in view of the provision of formulae IIa and IIb above. Of the joint possible compounds however, due to various factors and in particular steric hindrance, the two compounds where the amide group is on the opposite side of the molecule to the more bulky substituent $R_1$ or $R_2$ will predominate. It has been found that up to 90% of the product is a mixture of the two isomers where the above condition is met.

The various racemic mixtures can be resolved at appropriate stages by methods known in the art to the corresponding optically pure stereoisomers. Therefore, included within the scope of the present invention are the various possible isomers individually as well as the said racemic mixtures.

The process of the present invention may advantageously be carried out in a protic solvent and preferred are water or a lower alcohol such as methanol or ethanol. However, aprotic solvents, for example, ethers, such as ethyl ether, and aromatic solvents such as benzene and toluene, may also be used.

The following examples are provided by way of further illustrating, but not limiting, the present invention.

EXAMPLE I

Dimethylamine salt of 3-exo-carboxy-2-exo-dimethylcarboxmido-4-methyl-7-oxabicyclo-[2.2.1]-5-heptene (i.e., formula IIa above where $R_1=R_3=R_4=CH_3$ : $R_2=H$) 14.4 g. of the anhydride of 2,3-exo-dicarboxy-4-methyl-7-oxabicyclo-[2.2.1]-5-heptene were added en mass to a stirred solution comprising 18 ml. of 40% by volume aqueous dimethylamine and 100 ml. of methanol.

The reaction is slightly exothermic and the resulting mixture was stirred at the resulting temperature for a further 15 minutes or until a homogenous solution was obtained. The solvents were removed in vacuo and the residue recrystallized from acetone. The desired compound was obtained after filtration as white crystals which were washed with acetone. 17.85 G. of the desired compound was obtained, having a melting point of 112°C. (dec.) and was characterized further by IR and NMR data.

The mother liquors were found to contain a small amount of a mixture of the desired compound of formula IIa with IIb.

The compounds defined in the following table were prepared in an analogous manner to that described in Example 1 above, the various symbols used being referred to formula IIa above.

The inorganic salt compound of example 5 was formed by the exchange of an initially formed dimethylammonium ion for the sodium ion. This was effected by treatment of the product of Example 1 with exactly one molar equivalent of sodium methoxide in methanol. The resulting solution was evaporated and the residue recrystalized in the usual manner.

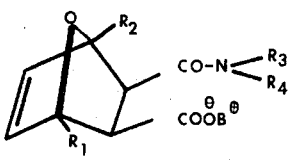

| Example No. | $R_1$ | $R_2$ | $R_3$ | $R_4$ | $B^+$ | M.P. | Structure Confirmed by: |
|---|---|---|---|---|---|---|---|
| 2 | $CH_3$ | H | H | H | $^+NH_4$ | 172–173°C | NMR |
| 3 | $CH_3$ | H | H | $(CH_2)_3-CH_3$ | $^+NH_3-(CH_2)_3-CH_3$ | 128–129°C | NMR |
| 4 | $CH_3$ | H | H | $(CH_2)_2-CH_3$ | $^+NH_3(CH_2)_2-CH_3$ | 120–122°C | NMR |
| 5 | $CH_3$ | H | $CH_3$ | $CH_3$ | $Na^+$ | 172–174°C | IR, NMR |

Further specific novel salts of formula IIa according to the present invention are contained in the following table.

| No. | $R_1$ | $R_2$ | $R_3$ | $R_4$ | $B^+$ |
|---|---|---|---|---|---|
| 6 | H | $CH_3$ | $CH_3$ | $CH_3$ | $H_2N^+(CH_3)_2$ |
| 7 | $CH_3$ | $CH_3$ | H | $CH_3$ | $K^+$ |
| 8 | $CH_3$ | H | \multicolumn{2}{piperidino} | piperidinium ($H_2$-$N^+$) |
| 9 | H | $CH_3$ | \multicolumn{2}{morpholino} | $Na^+$ |
| 10 | H | H | $CH_3$ | $CH_3$ | $H_2N^+(CH_3)_2$ |
| 11 | $CH_3$ | H | $CH_3$ | $-CH_2-C_6H_5$ | $H_2N^+(CH_3)(CH_2C_6H_5)$ |
| 12 | $CH_3$ | H | $CH_3$ | $CH_3$ | $H_2N^+(C_2H_5)(CH_3)$ |

The novel compounds of this invention (general formula II) can be used to prepare the derivatives of formula III:

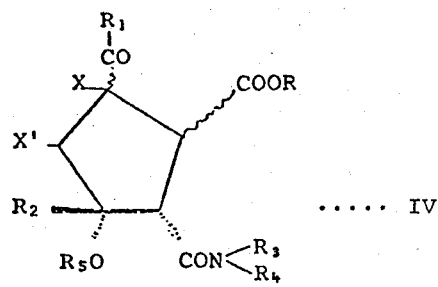

wherein

R and $R_2$ each individually represent a hydrogen atom or an alkyl group; $R_1$ represents an alkyl group; $R_3$ and $R_4$ each individually represent an alkyl or aralkyl group, or, together with the adjoining nitrogen atom form a heterocyclic ring which may include further heteroatoms such as oxygen or nitrogen; $—OR_5$ is a functional group; and X and X' represent hydrogen atoms or, when taken together, a double bond.

The compounds of formula IV have pharmacological, such as analgesic anti-inflammatory activity. Additionally, they are intermediates in the production of other pharmacologically active compounds such as some prostaglandin-type compounds sharing the same cyclic moiety.

As stated $—OR_5$ is a functional group where $R_5$ is for example, hydrogen, alkyl, acyl, carbamoyl and so on. The alkyl groups $R_1$ to $R_5$ which may be straight chain or branched, are preferably lower alkyl groups having 1 to 6 and especially 1 to 4 carbon atoms. Examples of such groups are methyl, ethyl, and the various propyl, butyl, pentyl and hexyl groups. The aralkyl group as $R_3$ and $R_4$ preferably has 1 to 6, especially 1 to 4 carbon atoms in the alkyl moiety, the aryl moiety including especially the phenyl group; acyl group $R_5$ may have the formula alkyl-CO- where alkyl is as defined above. Carbamoyl group $R_5$ preferably has the formula:

$R_6$—NHCO— where $R_6$ is an alkyl group as defined above or an aryl group, for example, phenyl or a phenyl substituted by halogen, such as chlorine or bromine; nitro; or $CF_3$.

It will be noted that formula IV includes cyclopentene and cyclopentane derivatives. The cyclopentene derivatives of the present invention are generally of formula Va and Vb Va

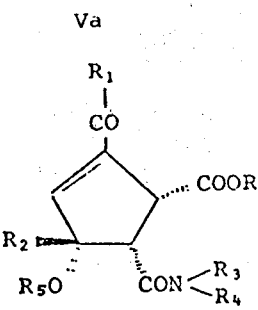

Vb

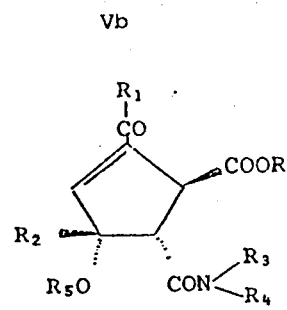

The cyclopentane derivatives of the present invention fall generally within one of the following formulae:

VIa

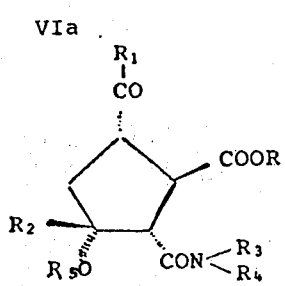

VIb

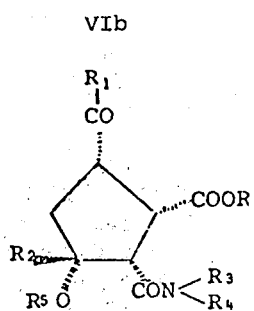

VIc

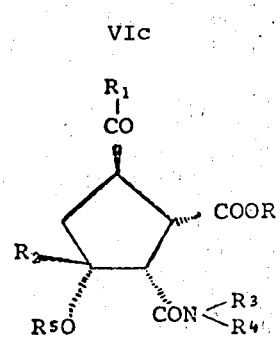

In these formulae, symbols $R_1$ to $R_5$ are as defined above.

The various compounds represented by formula IV may be prepared from a starting material which is a γ-lactone of formula VII

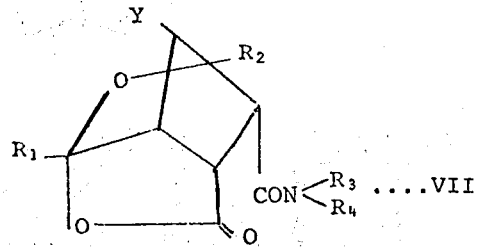

wherein $R_1$ to $R_4$ are as defined above; and
Y is halogen such as chlorine or bromine; by opening the lactone ring thereof with a, preferably, strong base such as an alkoxide like sodium methoxide. Preferably one mole-equivalent of the base is used.

The directly formed compounds falling within formula IV above, and in particular within formula Va, are then used to prepare the remaining compounds of the present invention. Ring opening of the lactone ring of the compound of formula VII produces the cis-syn epimer of formula Va wherein $R_5$ is hydrogen. The term syn throughout this specification always referring to the steric configuration of the -$OR_5$ group.

This compound may be converted into compounds having other functional groups in the 5- position by suitable known procedures. For example, acetylation using for example, an acyl halide such as acetyl chloride, produces the 5-acyl, and in that particular case, the 5-acetyl derivative of the said 5-hydroxy-epimer; a suitable isocyanate, such as a phenyl or alkyl-isocyanate produces a 5-urethane derivative. Compounds having an ether function in the 5-position may be prepared by alkylating using an alkyl halide such as methyl iodide, or dimethyl sulphate, especially by reaction with the sodium salt of the 5-hydroxy epimer, the sodium salt being formed for example, by reacting the 5-hydroxy compound with sodium hydride. In some cases it may be advisable to protect the keto function in the molecule prior to alkylating. This may be effected by forming the corresponding ketal which grouping is removed subsequent to the ether formation by hydrolysis using, for example, an acid such as HCl.

The cis-syn epimer of formula Va formed upon initial ring opening of the lactone of formula VII may be converted to the corresponding trans-syn epimer of formula IIb by any suitable method, such as treatment with a solution of an alkoxide, for example, sodium methoxide, in an alcohol such as methanol, optionally with protection of the keto group as described above.

The cyclopentane derivatives falling within formula IV i.e., those compounds of formulae VI a, b and c may be produced from the cyclopentene derivatives by, for example, hydrogenation using hydrogen gas in the presence of a hydrogenation catalyst such as platinum or palladium on carbon.

It should be noted that the conversion of the initially formed hydroxyl in the 5-position into another reactive function may usually be effected at any stage in a reaction sequence although care should be taken to avoid a reaction sequence which utilizes a reaction step where deleterious effects on groups or moieties already present in the molecule may be expected.

The starting lactones of formula VII may be prepared via a Wagner-Meerwein rearrangement, by halogenating, especially chlorinating or brominating a salt derivative of formula II

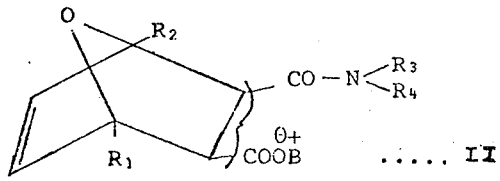

wherein $R_1$, $R_2$, $R_3$, $R_4$ and B are as defined above.

The novel derivatives of formula I and a process for their production are fully described above.

The active compounds of formula IV, re composition of matter aspects, can be used in pharmaceutical composition comprising as active ingredient at least one active compound of the general formula IV in association with a pharmaceutically acceptable carrier therefor.

The compositions of formula IV preferably administered either orally, parenterally or rectally. Advantageously, the composition is in a dosage unit form appropriate to the desired mode of administration. For example, the dosage unit may be a tablet, capsule, pill, powder, packet, granule, wafer, elixir, suppository, or a measured quantity of a suspension, solution, a syrup or segregated multiples of the foregoing. The term "dosage unit form" as used in the specification and claims refers to physically discrete units suitable as unitary dosages for human subjects and animals, each unit containing a predetermined quantity of active material calculated to produce the desired therapeutic effect in admixture, or otherwise in association, with a pharmaceutical carrier therefor, the quantity of the active ingredient being such that one or more units are normally required for a single therapeutic administration or that, in the case of severable units such as scored tablets, at least one fraction such as a half or a quarter of a severable unit is required for a single therapeutic administration.

The actual percentage of the active component in the composition may be varied, but advantageously is between about 2% and about 60%, or more, based on the total weight of the composition. Conveniently, the composition of the invention when in dosage unit form contains 0.5 mg. to 1000 mg., and more conveniently form 5 mg. to 250 mg., of the active ingredient of the general formula IV.

The compositions of the present invention will normally consist of at least one compound of formula IV, admixed with a carrier, or diluted by a carrier, or enclosed or encapsulated by a carrier in the form of a capsule, sachet, catchet, paper or other container. A carrier which serves as a vehicle, excepient or diluent medium for the therapeutically active ingredient may excipient a solid, semisolid or a sterile liquid.

Some examples of the carriers which may be employed in the pharmaceutical compositions of the invention are lactose, dextrose, sorbitol, mannitol, starches such as wheat, corn, or potato starch, gum acacia, calcium phosphate, liquid paraffin, cocoa butter, oil of theobroma, alginates, tragacanth, gelatin, syrup B.P., methyl cellulose, polyoxethylene sorbitan monolaurate, methyl and propyl hydroxybenzoates, pyrogen-free water and substantially isotonic saline solution. The choice of carrier is determined by the preferred form of administration, the solubility of the compound and standard pharmaceutical practice, all as more clearly set forth in "Remington's Practice of Pharmacy" by E. W. Martin and E. F. Cook, a well-known reference text in this field.

In the case of tablets, a lubricant may be incorporated to prevent sticking and binding of the powdered ingredients in the dies and on the punch of the tabletting machine. For such purpose, there may be employed, for example, talc, aluminum, magnesium or calcium stearates or polyethylene glycols (Carbowaxes) of suitable molecular weight.

The pharmaceutical compositions of this invention may contain, in addition to the active ingredient of the general formula IV, one or more other pharmacologically active ingredients which elicit desirable complementary effects.

An example of suitable pharmaceutical compositions according to this invention are presented below for the purpose of facilitating a better understanding of this aspect of the invention.

EXAMPLE 13

For oral administration, sugar coated tablets may have the following composition:

| Formulation: Ingredient | Ingredient (mg) |
| --- | --- |
| Trans-anti-cis-1 acetyl-2 carbomethoxy-3-dimethylcarboxamido-4-acetoxy-cyclopentane | 25 mg |
| Lactose | 60 |
| Starch | 50 |
| Sugar | 75 |
| Talc | 5 |
| Gum arabic | 5 |

The present invention will be further described but not limited to the following specific examples.

Description of preparation of γ-lactones of Formula VII

The γ-lactones of Formula VII defined in the following Table 3 were prepared in a similar manner to the procedure described in Step (ii) of Example 14 starting of course from the corresponding amine salt.

EXAMPLE 14

Preparation of γ-lactone of 7-bromo-5-endocarboxy-6-endo-dimethylcarboxamide-3-endo-hydroxy-3-exomethyl-2-oxabicyclo-[2.2.1] heptane. (Formula IV wherein $R_1=R_3=R_4=CH_3$; $R_2=H$; Y=Br)

(i) From the dimethylamine salt of 3 exo-carboxy 2 exo-dimethylcarboxamido-4-methyl-7-oxabicyclo[2.2.1]-5-heptene A well stirred solution of 15.75 g. of the dimethylamine salt of 3-exo-carboxy-2 exo-dimethylcarboxamido-4-methyl-7-oxabicyclo [2.2.1]-5-heptene in 200 ml. of water was cooled to about 1°C. in an ice bath and 9.3 g. of bromine vapour was passed into said cooled solution over 30 minutes via a stream of nitrogen. The temperature of the solution during the bromine addition was maintained between 0°-5°C. The precipitated solid was separated by filtration, washed with cold water and whilst still wet, suspended in 75 ml. of cold acetone and subsequently refiltered. 13.2 G. of white crystalline crude product having a melting point of 126°C. was obtained. The product was recrystallized using acetone (excess acetone being removed in vacuo at 30°C.), the melting point of the recrystallized product being 131°C. (dec.).

(ii) From the amine salt as in (i) but which salt is prepared in situ from the anhydride of 2.3 exo-dicarboxy-4-methyl-7-oxabicyclo [2.2.1]-5-heptene and not isolated prior to its being converted to the desired lactone.

36 G. of the anhydride of 2,3 exo-dicarboxy-4-methyl-7-oxabicyclo [2.2.1]-5-heptene was added at room temperature to a stirred solution of 18 g of dimethylamine dissolved in 420 ml. of water, and the mixture stirred at that temperature for about twenty minutes, i.e. until all the solid dissolved. The mixture was then cooled to 0° – 1°C. and 32 g. of bromine vapour passed thereinto via a stream of air or nitrogen. The temperature during the addition of the bromine was maintained at between 0° and 5°C. The addition of the bromine took about 45 minutes and the solid which precipitated was filtered using suction and washed with 100 ml. of cold water. The wet material was suspended in 175 ml. of cold methanol, refiltered using suction and washed with methanol. 46.5 G. of a creamy crystalline product comprising mainly the desired compound but contaminated with a small amount of isomer where $R_1$ and $R_2$ are interchanged was obtained. Upon recrystallizing the crude product by dissolving same in 1350 ml. of refluxing methanol and allowing to cool, 32.3 g. of the desired product was obtained in the form of white crystals - melting at 131°C. (dec.). The structure was further confirmed by IR and NMR spectral analysis.

of abs. methanol. The exothermic reaction was subjected to cooling with dry-ice/acetone bath at such a rate that the sodium methoxide addition took 4 – 5 minutes while the reaction temperature was maintained between 4° and 10°C. Upon completing the reaction the pH was then checked and if found to be basic, adjusted to neutral using a few drops of acetic acid. The methanol was removed in vacuo and the residue treated with chloroform. The insoluble sodium bromide was removed by filtration and the solvent removed by evaporation to dryness in vacuo. The residue was crystallized from ethyl acetate/ether, separated by filtration and washed with a small amount of cold ethyl acetate. 95 G. of the desired product having a melting point of 98° – 102°C. was obtained. Recrystallization from ethylacetate gave 90 g. of purified compound, melting point 105° – 106°C.

EXAMPLE 24

Preparation of 2-acetyl-trans-syn-3-carbomethoxy-4-dimethylcarboxamido-5-hydroxy-1-cyclopentene.

A mixture of 30 g. of 2-acetyl-cis-syn-3 carbomethoxy-4-dimethylcarboxamido-5-hydroxy-1-cyclopentene in 200 ml. of ethyl acetate was brought to reflux and a solution of 0.22 g. sodium methoxide in 2 ml. of methanol was added thereto at once and the reflux continued for six minutes. The reaction mixture was then rapidly cooled using an ice bath until its temperature was approximately 40° – 45°C. when about 100 ml. of the solvent was removed in vacuo. The resulting reaction mixture was cooled in an ice bath for thirty minutes resulting in the crystallization of the product Table 3

| Example No. | $R_1$ | $R_2$ | $R_3$ | $R_4$ | X | M.P. (°C) | Structure Confirmed by: |
|---|---|---|---|---|---|---|---|
| 15 | $CH_3$ | H | $C_2H_5$ | $C_2H_5$ | Br | 120° (dec.) | IR,NMR |
| 16 | $CH_3$ | H | |  | Br | 131° (dec.) | IR,NMR |
| 17 | $n-C_3H_7$ | H | $CH_3$ | $CH_3$ | Br | 118° (dec.) | IR,NMR |
| 18 | H | H | |  | Br | — | IR,NMR |
| 19 | $CH_3$ | H | $CH_3$ | $-CH_2-\phi$ | Br | 145° (dec.) | IR,NMR |
| 20 | $CH_3$ | $CH_3$ | $CH_3$ | $CH_3$ | Br | * | IR,NMR |
| 21 | $CH_3$ | H | H | H | Br | * | IR,NMR |
| 22 | $CH_3$ | H | $CH_3$ | $CH_3$ | Cl | 195°–196° (dec.) | IR,NMR |

* M.P. dependent on rate of heating

The following Examples 23 to 31 describe in detail the production of specific compounds of Formula IV both directly and indirectly, from the novel lactones of Formula VII. The various procedures described in these examples are applicable, obviously with appropriate changes of starting materials, etc., to the preparation of the compounds of Formula IV given in the following Tables 4 to 7.

EXAMPLE 23

Preparation of 2-acetyl-cis-syn-3-carbomethoxy-4-dimethylcarboxamido-5-hydroxy-1-cyclopentene.

A solution of 27 g. of sodium methoxide in 200 ml. of abs. methanol was added dropwise to a stirred suspension of 152 g. of the γ-lactone of Example 13 in 600 ml.

which was collected by filtration and washed with cold ethyl acetate. 10.8 G. of this crude product melting at 135° – 138°C. was obtained. Upon recrystallization from hot ethyl acetate, 10.1 g. of refined product having a melting point of 141° – 142°C. was obtained.

The combined mother liquors from the above procedure were concentrated to 100 ml. volume, heated to reflux, and a solution of 0.11 g. sodium methoxide in 1 ml. of methanol was added. The above procedure was repeated but only 50 ml. of ethyl acetate was removed. In this way a further 4.1 g. of the crystallized desired product was obtained having a melting point of 140° – 142°C.

EXAMPLE 25

Preparation of 2-acetyl-trans, syn-3-carbomethoxy-4-dimethylcarboxamido-5-acetoxy-1-cyclopentene.

A mixture of 1.2 g. of 2-acetyl-trans, syn-3-carbomethoxy-4-dimethylcarboxamido-5-hydroxy-1-cyclopentene, 12 ml. of methylene chloride and 1.2 ml. of acetyl chloride were refluxed for 30 minutes under anhydrous conditions, atmospheric moisture being excluded from the apparatus by a calcium chloride drying tube. The volatile components of the reaction mixture were then removed in vacuo and the residue crystallized from ether and recrystallized from ethylacetate. The desired product was obtained in a yield of 1.1 g. and the white crystals had a melting point of 112°–114°C.

EXAMPLE 26

Conversion of "cis, syn" isomer to "trans, syn" isomer utilizing a protected keto group procedure.

(i) A mixture of 25.5 g. of 2-acetyl-cis, syn-3-carbomethoxy-4-dimethylcarboxamido-5-hydroxy-1-cyclopentene, 200 ml. of dry benzene, 15 ml. of ethylene glycol and 0.3 g. of p-toluenesulphonic acid monohydrate was gently refluxed for 17 hours and the water collected in a Dien-Stark apparatus. The reaction mixture was cooled to room temperature, 3 ml. of triethylamine was added and the mixture washed with 50 ml. of water which was subsequently saturated with sodium chloride and extracted twice with 50 ml. of methylene chloride. The benzene solution and methylene chloride extracts were combined, dried over sodium sulphate and evaporate when 21.8 g. of the desired ketal of the above cis, syn isomer was obtained as a white solid melting at 82° – 83°C.

(ii) 0.55 G. of sodium methoxide was added to a solution comprising 16.5 g. of the ketal formed in (i) in 100 ml. of methanol. The mixture was rapidly heated to reflux which was continued for three minutes, after which it was cooled in an ice bath to room temperature and the pH adjusted to neutral with acetic acid. The methanol was then removed by evaporation, 25 ml. of water added and the mixture extracted with 100 ml. methylene chloride. The aqueous phase was saturated with sodium chloride and extracted twice with 50 ml. of methylene chloride, the combined organic phase then being dried over sodium sulphate and evaporated. The crude ethylene ketal of 2-acetyl-trans, syn-3-carbomethoxy-4-dimethylcarboxamido-5-hydroxy-1-cyclopentene was crystallized from ether end recrystallized from ethylacetate, the product then having a melting point of 87° – 89°C.

Yield: 12 g.

(iii) Removal of ketal group.

A solution comprising 10 g. of the ketal formed in (ii) in 100 ml. of methanol was added to 100 ml. of water containing 1 ml. of conc. hydrochloric acid. The combined solution was allowed to stand at room temperature for three days. The solution was then neutralized with sodium bicarbonate and evaporated, a minimum amount of water added and the solution extracted exhaustively with methylene chloride; dried over sodium sulphate, filtered and finally evaporated in vacuo. The product was obtained in the form of crystals from ether and subsequently recrystallized from ethyl acetate. The desired product, obtained in a yield of 6.1 g., had a melting point of 140° – 142°C. and its structure confirmed by NMR analysis.

EXAMPLE 27

Production of a urethane derivative

To a solution of 0.6 g. of 2-acetyl-trans-syn-3-carbomethoxy-4-dimethylcarboxamido-5-hydroxy-1-cyclopetene in 6 ml. of benzene was added 0.3 g. of phenylisocyanate, and the solution refluxed for 1.5 hours. The precipitate which formed was filtered off and washed with benzene. The yield was 0.6 g. and the product had a melting point of 183° – 185°C.

EXAMPLE 28

Conversion of a cyclopentene derivative to a cyclopentane derivative by hydrogenation 0.1 G. amount of 5% palladium on carbon was added to a solution comprising 3 g. of 2-n-butyryl-cis-syn-3-carbomethoxy-4-dimethylcarboxamido-5-hydroxy-1-cyclopentene in 50 ml. of absolute methanol. The mixture was hydrogenated at 50 lbs. per sq. inch pressure until take up of hydrogen ceased. The catalyst was removed by filtration. The methanol was evaporated in vacuo and the residue treated with ether. The resulting solid was filtered off and retreated with ether to produce crystals which were filtered off and washed with ether. The yield of the product, which had a melting point of 80° – 81°C. was 2.5 g.

EXAMPLE 29

Epimerization, at the ketone function, to convert cis-syn-cis compound to the corresponding trans-syn-cis compound.

A solution of 3.0 g. of cis-syn-cis-1-acetyl-2-carbomethoxy-3-dimethylcarboxamido-4-hydroxy-cyclopentane in 30 ml. of methanol containing 6.0 ml. of triethylamine was allowed to stand at room temperature overnight. The resulting solution was evaporated in vacuo and the residue treated with ether. The product, obtained in a yield of 2.0 g., had a melting point of 74° – 77°C. Upon recrystallization three times from ethyl acetate the melting point improved to 80° – 82°C.

EXAMPLE 30

Production of an acid derivative of Formula I, i.e. wherein R is hydrogen.

A solution comprising 0.48 g. of sodium hydroxide in 5 ml. of water was added to a solution of 2.55 g. trans-anti-cis-1-acetyl-2-carbomethoxy-3-dimethylcarboxamido-4-hydroxycyclopentane in 10 ml. of water and maintained at room temperature for three hours. The resulting solution was poured onto 90 Dowex g. of Lowex 50 W-X8 ion exchange resin, which had previously been washed to neutrality with distilled water, and the mixture stirred well. An acidic mixture resulted which was filtered, washed with water and evaporated in vacuo. The residue was taken up in ether and the desired acid product obtained as crystals having a melting point of 118° – 120°C. in a yield of 1.8 g. The structure was confirmed by spectral analysis in the normal manner.

EXAMPLE 31

Etherification of the 5-position hydroxyl group utilizing a ketal protected ketone function.

15.7 g. of the ethylene ketal of trans-anti-cis-1 acetyl-2-carbomethoxy-3-dimethylcarboxamido-4-hydroxy-cyclopentane dissolved in 150 ml. of benzene was added slowly to a stirred suspension of 2.1 g. sodium hydride (57% oil dispersion) which had previously been washed with 2 × 10 ml. of benzene. Formation of the sodium salt was allowed to proceed for 5 minutes at room temperature or until hydrogen evolution ceased. 25 Ml. of methyl iodide was added and the reaction medium allowed to stand at room temperature for 30 minutes; the reaction was completed by heating on a 60°C. water bath for 3 minutes. The mixture was then cooled and 15 ml. of water added. The organic layer was separated and the aqueous layer extracted with 2 × 75 ml. of methylene chloride. The combined organic fractions were dried over sodium sulphate, filtered and evaporated in vacuo. The residue was treated with minimum ether for dissolution and cooled in a refrigerator. The resulting product, containing a methoxy group in the 5-position and a ketal protected keto function was obtained in a yield of 9.7 g. and had a melting point of 85° – 86°C. This compound was treated in the manner described in Example 26 (iii) to remove the ketal group thereby regenerating the keto function. The keto product also had a melting point of 85° to 86°C.

As stated previously the following Tables contain further specific examples of compounds of the general formula IV according to the present invention. The actual procedure used to produce each compound is indicated in each Table.

Table 4

Compounds for Formula IIa

| | Example No. | R | $R_1$ | $R_2$ | $R_3$ | $R_4$ | $R_5$ | M.P. | Structure Confirmed by: |
|---|---|---|---|---|---|---|---|---|---|
| * | 23 | $CH_3$ | $CH_3$ | H | $CH_3$ | $CH_3$ | H | 105°–106° | IR,NMR |
| + | 32 | $CH_3$ | $CH_3$ | H | $CH_3$ | $CH_3$ | $CH_3CO-$ | 72°–74° | IR,NMR |
| ++ | 33 | $CH_3$ | $CH_3$ | H |  | | H | 112°–114° | IR,NMR |
| ++ | 34 | $CH_3$ | n-$C_3H_7$ | H | $CH_3$ | $CH_3$ | H | 116°–117° | IR,NMR |
| ++ | 35 | $CH_3$ | $CH_3$ | $CH_3$ | $CH_3$ | $CH_3$ | H | 138°–139° | IR,NMR |
| ++ | 36 | $CH_3$ | $CH_3$ | H |  | | H | 130°–131° | NMR |
| + | 37 | $CH_3$ | $CH_3$ | H |  | | $CH_3CO-$ | 125°–128° | NMR |

\* Descriptive example
++ Formed by ring opening according to the procedure of example 14(ii) of the corresponding γ-lactones.
+ Formed by acetylation according to the procedure of example 25 of the corresponding hydroxy-compound.

Table 5

Compounds for Formula IIb

| | Example No. | R | $R_1$ | $R_2$ | $R_3$ | $R_4$ | $R_5$ | M.P. | Structure Confirmed by: |
|---|---|---|---|---|---|---|---|---|---|
| * | 24 | $CH_3$ | $CH_3$ | H | $CH_3$ | $CH_3$ | H | 140°–142° | IR,NMR |
| * | 25 | $CH_3$ | $CH_3$ | H | $CH_3$ | $CH_3$ | $CH_3CO-$ | 112°–114° | NMR |
| + | 38 | $CH_3$ | $CH_3$ | H | $CH_3$ | $CH_3$ | $\phi-NH-CO-$ | 183°–185° | NMR |
| + | 39 | $CH_3$ | $CH_3$ | H | $CH_3$ | $CH_3$ | $\begin{array}{c}CH_3\\ >CHNHCO-\\ CH_3\end{array}$ | 110°–112° | NMR |
| ** | 40 | $CH_3$ | $CH_3$ | H |  | | H | 150°–154° | IR,NMR |
| ** | 41 | $CH_3$ | $CH_3$ | H |  | | $CH_3CO-$ | 119°–120° | IR,NMR |
| ++ | 42 | $CH_3$ | n-$C_3H_7$ | H | $CH_3$ | $CH_3$ | H | 120°–122° | IR,NMR |
| ++ | 43 | $CH_3$ | $CH_3$ | H |  | | H | 185°–187° | NMR |
| ** | 44 | $CH_3$ | $CH_3$ | H |  | | $CH_3CO-$ | 99°–100° | NMR |

Table 5-continued

Compounds for Formula IIb

| | Example No. | R | $R_1$ | $R_2$ | $R_3$ | $R_4$ | $R_5$ | M.P. | Structure Confirmed by: |
|---|---|---|---|---|---|---|---|---|---|
| ++ | 45 | $CH_3$ | $CH_3$ | $CH_3$ | $CH_3$ | $CH_3$ | H | 123°–124° | NMR |

\* Descriptive example
\*\* Formed by acetylation according to the procedure of example 25 of the corresponding hydroxy compounds.
\+ Formed by reaction of the corresponding hydroxy compound and a suitable isocyanate according to the procedure of example 27
++ Formed by epimerization of the ester function of the corresponding-compound of formula IV by the procedure of example 24

TABLE 6

Trans-anti-cis compounds for formula IIIa

| | Example No. | R | $R_1$ | $R_2$ | $R_3$ | $R_4$ | $R_5$ | M.P. | Structure Confirmed by: |
|---|---|---|---|---|---|---|---|---|---|
| + | 46 | $CH_3$ | $CH_3$ | H | $CH_3$ | $CH_3$ | $CH_3CO-$ | 112°–114° | IR,NMR |
| + | 47 | $CH_3$ | $CH_3$ | H | $CH_3$ | $CH_3$ | H | 79°–80° | IR,NMR |
| \*\* | 48 | $CH_3$ | $CH_3$ | H | $CH_3$ | $CH_3$ | $\phi-NH-CO-$ | 171°–173° | NMR |
| \*\* | 49 | $CH_3$ | $CH_3$ | H | $CH_3$ | $CH_3$ | $CH_3$-CH-NH-CO- | 70°–71° | NMR |
| + | 50 | $CH_3$ | $n-C_3H_7$ | H | $CH_3$ | $CH_3$ | $CH_3CO-$ | — | NMR |
| \* | 30 | H | $CH_3$ | H | $CH_3$ | $CH_3$ | H | 118°–120° | IR |
| \* | 31 | $CH_3$ | $CH_3$ | H | $CH_3$ | $CH_3$ | $CH_3$ | 85°–86° | NMR |

\+ Formed by hydrogenation according to the precedure of example 28 of the compounds of examples 25 24 and 42 respectively.
\*\* Formed by reaction of the appropriate isocyanate with the compound of example 47 according to the precedure of example 27
\* Descriptive example

TABLE 7

Cis-syn-cis compounds of formula IIIb

| Example No. | R | $R_1$ | $R_2$ | $R_3$ | $R_4$ | $R_5$ | M.P. | Structure Confirmed by: |
|---|---|---|---|---|---|---|---|---|
| 51 | $CH_3$ | $n-C_3H_7$ | H | $CH_3$ | $CH_3$ | H | 80°–81° | NMR |
| 52 | $CH_3$ | $CH_3$ | $CH_3$ | $CH_3$ | $CH_3$ | H | 102°–103° | NMR |

TABLE 8

Trans-syn-cis compounds of formula IIIc

| | Example No. | R | $R_1$ | $R_2$ | $R_3$ | $R_4$ | $R_5$ | M.P. | Structure Confirmed by: |
|---|---|---|---|---|---|---|---|---|---|
| + | 53 | $CH_3$ | $CH_3$ | H | $CH_3$ | $CH_3$ | $CH_3CO-$ | | IR,NMR |
| \* | 16 | $CH_3$ | $CH_3$ | H | $CH_3$ | $CH_3$ | H | 80°–82° | IR,NMR |
| + | 54 | $CH_3$ | $CH_3$ | H | (tetrahydropyranyl) | | H | | |
| + | 55 | $CH_3$ | $CH_3$ | H | (cyclohexyl) | | H | 121°–122° | NMR |
| ++ | 56 | $CH_3$ | $CH_3$ | H | (tetrahydropyranyl) | | $CH_3CO-$ | 141°–142° | NMR |
| ++ | 57 | $CH_3$ | $CH_3$ | H | (cyclohexyl) | | $CH_3CO-$ | 78°–79° | NMR |

\* Descriptive example
\+ Formed by epimerization at the ketone function according to the procedure of example 16 of the compounds of examples 46, 43 and 40, respectively.
++ Formed by acetylation according to the precedure of example 25 of the corresponding hydroxy compound of example 54 and 55

We claim:
1. A 2,3-di-exo-substitute 7-oxabicyclo-[2.2.1]-5-heptene derivative of the formula:

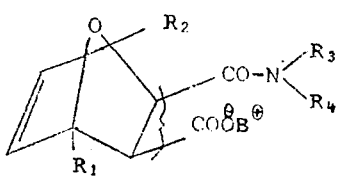

wherein $R_1$ and $R_2$ each individually represent a hydrogen atom or a lower alkyl;

$R_3$ and $R_4$ each individually represent a hydrogen atom or a lower alkyl; and B represents an ammonium ion of the formula:

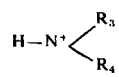

where $R_3$ and $R_4$ are defined above and the sodium cation.

2. The dimethylamine salt of 3-exo-carboxy-2-exo-dimethylcarboxamido-4-methyl-7-oxabicyclo-[2.2.1]-5-heptene.

3. The ammonium salt of 3-exo-carboxy-2-exo-carboxamido-4-methyl-7-oxabicyclo-[2.2.1]-5-heptene.

4. The n-butylamine salt of 3-exo-carboxy-2-exo-di-n-butylcarboxamido-4-methyl-7-oxabicyclo-[2.2.1]-5-heptene.

5. The n-propylamine salt of 3-exo-carboxy-2-exo-di-n-propylcarboxamido-4-methyl-7-oxabicyclo-[2.2.1]-5-heptene.

6. The sodium salt of 3-exo-carboxy-2-exo-dimethylcarboxamido-4-methyl-7-oxabicyclo-[2.2.1]-5-cycloheptene.

* * * * *